US00PP13497P2

(12) United States Plant Patent
Bradford

(10) Patent No.: US PP13,497 P2
(45) Date of Patent: Jan. 21, 2003

(54) PLUM TREE NAMED 'RED MAJESTY'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/014,024

(22) Filed: Dec. 13, 2001

(51) Int. Cl.[7] ..... A01H 5/00
(52) U.S. Cl. ..... Plt./184; Plt./185
(58) Field of Search ..... Plt./184, 185

*Primary Examiner*—Bruce R. Campell
*Assistant Examiner*—W C Haas

(57) ABSTRACT

The present invention relates to a plum tree, *Prunus salicina*, and more particularly to a new and distinct variety broadly characterized by a medium size, vigorous, hardy, self-unfruitful, and productive tree. The fruit matures under the ecological conditions described approximately the third week in June, with first picking on Jun. 19, 2001. The fruit is uniformly large in size, good in flavor, oblate in shape, clingstone in type, spongy in texture, yellow in flesh color, and bright red in skin color. The variety was developed from an open pollinated seed from an unnamed red plum.

1 Drawing Sheet

CROSS REFERENCE TO RELATED APPLICATIONS

This case is related to co-pending U.S. Plant patent application Ser. No. 10/014,023, filed Dec. 13, 2001, drawn to 'YUMMYGIANT' plum.

BOTANICAL CLASSIFICATION

*Prunus salicina.*

BACKGROUND OF THE VARIETY

In a continuing effort to improve the quality of shipping fruits, I, the inventor, typically hybridize a large number of nectarine, peach, plum, apricot, and cherry seedlings each year. In an effort to exhibit recessive traits, I also grow a lesser number of open pollinated seeds of each of these fruits. In my breeding grounds during the summer of 1992 I regularly gathered open pollinated seeds from several different unpatented plum trees which bore red plums. This group of seeds, designated as "Red Plum (OP)", was germinated and grown as seedlings on their own root in my greenhouse and transplanted to a cultivated area of my experimental orchard at Bradford Farms near Le Grand, Calif. in Merced County (San Joaquin Valley).

The present invention relates to a new and distinct variety of plum tree, which has been denominated varietally as 'RED MAJESTY'. It was selected by me during the 1997 fruiting season as a single plant from the group of open pollinated seedlings described above. Subsequent to origination and selection of the present variety of plum tree, I asexually reproduced it by budding and grafting in the experimental orchard described above, and such reproduction of plant and fruit characteristics were true to the original plant in all respects. The reproduction of the variety included the use of 'Nemaguard' Rootstock (unpatented) upon which the present variety was compatible and true to type.

The present variety is similar to 'Santa Rosa' (unpatented) by producing red plums that harvest in late June, but is distinguished therefrom and an improvement thereon by producing fruit that is larger in size, axially compressed in shape, and matures about 8 days earlier. Contrary to the 'Santa Rosa', the present variety is self-unfruitful and must be cross pollinated by other plums. Two acceptable pollinators are 'Laroda' (unpatented) and 'Wickson' (unpatented). Also, the variety produces an abundance of pollen, which attracts bees to facilitate the cross pollination.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif., and was developed when the fruit was firm ripe on Jun. 22, 2001, on the original tree during its ninth growing season. All major color code designations are by reference to the Inter-Society Color Council, National Bureau of Standards. Common color names are also used occasionally.

TREE

Size: Medium, reaching and maintaining a height of 13' [3.96 m.] after nine growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commerical rootstock for production purposes.

Growth: Upright and dense.

Form: Vase formed.

Hardiness: Hardy with respect to central California winters.

Heat tolerance: Observed to perform adequately in typical central California climatic conditions, which typically include prolonged periods of heat.

Drought tolerance: Variety is developed for commercial orchards and requires regular irrigation.

Production: Productive, thinning usually necessary.

Fertility: Self-unfruitful, requiring cross pollination by a suitable pollinator, such 'Laroda' (unpatented) or 'Wickson' (unpatented).

Bearing: Regular bearer except for years with excessive rain during the bloom season.

Trunk:

*Size*.—Medium, reaching a maximum diameter fo 4.5" [114 mm.] after the ninth growing season.

*Texture*.—Rough.

*Bark color*.—Grayish brown [61. gy.Br] with Light brown [57. l.Br.] streaking.

*Lenticels*.—Numerous. Color: Brownish orange [54. brO]. Average Size: ¼" [6.4 mm.].

Branches:

*Size*.—Diameter of scaffold is 2¼" [57 mm.] measured 12" above the crotch, typical of *Prunus salicina*, and dependent upon cultural practices and climatic conditions.

*Texture*.—Smooth on 1st year wood, increasing roughness with age.

*Color*.—1st Year Wood Topside: Dark grayish red [20. d.gy.R]. 1st Year Wood Underside: Strong yellow green [117. s.YG]. 2nd Year Wood: Deep brown [56. deepBr]. Older Wood: Dark grayish brown [62. d.gy.Br].

*Lenticels*.—Numerous. Color: Strong yellowish brown [74. s.yBr]. Average Size: ⅛" [3.2 mm.].

Leaves:

*Size*.—Medium. Average Length: 4½" [114 mm.]. Average Width: 1⅞" [48 mm.].

*Arrangement*.—Alternate.

*Thickness*.—Medium.

*Form*.—Elliptical.

*Apex*.—Acuminate.

*Base*.—Rounded to somewhat acute with an average angle of 90 degrees.

*Surface*.—Smooth.

*Color*.—Dorsal Surface: Moderate olive green [125. m.OlG]. Ventral Surface: Moderate yellow green [120. m.YG].

*Margin*.—Finely serrate.

*Venation*.—Pinnately net veined.

*Petiole*.—Average Length: 9/16" [14.3 mm.]. Average Thickness: 1/16" [1.6 mm.]. Color: Light yellow green [119. l.YG].

*Stipules*.—Up to 2 per leaf, up to 6 per growing tip. Average Length: ⅜" [9.5 mm.]. Color: Light yellow green [119. l.YG] becoming Deep yellowish brown [75. deep yBr] with age.

*Glands*.—Number: Usually 2 per leaf. Position: Mostly alternate, positioned on the petiole very close to the base of blade. Size: Small. Form: Globose. Color: Light yellow green [119. l.YG] forming Dark reddish brown [44. d.rBr] centers with age.

*Leaf buds*.—Pointed.

Flower buds:

*Hardiness*.—Hardy, with respect to central California winters.

*Diameter*.—Typically 3/16" [4.8 mm.] 1 week before bloom.

*Length*.—Typically 5/16" [7.9 mm.] 1 week before bloom.

*Form*.—Not appressed.

*Surface*.—Pubescent.

*Color*.—White [263. White].

Flowers: Perfect, complete, perigynous, usually a single pistil, typically twenty-four or more stamens, five sepals and petal locations alternately positioned.

*Number per cluster*.—1 to 9, average is 5.

*Average flower diameter*.—13/16" [20.6 mm.].

*Number of petals*.—Five.

*Petal shape*.—Oval.

*Petal margin*.—Slightly wavy.

*Average petal diameter*.—¼" [6.4 mm.].

*Average petal length*.—⅜" [9.5 mm.].

*Petal apex*.—Rounded.

*Petal base*.—Rounded.

*Petal color*.—White [263. White].

*Anther color*.—Brilliant orange yellow [67. brill.OY].

*Stigma color*.—Brilliant greenish yellow [98. brill. gY].

*Sepal color*.—Grayish purplish red [262. gy.pR].

*Sepal length*.—5/32" [4 mm].

*Sepal width*.—5/32" [4 mm].

*Average pistil length*.—7/16" [11.1 mm.].

*Average stamen length*.—⅜" [9.5 mm.].

*Fragrance*.—Moderate when nectar is present.

*Blooming period*.—Medium when compared with other varieties, 2 days after 'Santa Rosa' in 2001.

*Onset of bloom*.—One percent on Feb. 23, 2001.

*Date of full bloom*.—Mar. 5, 2001.

*Duration of bloom*.—One to two weeks, dependent on ambient temperature.

FRUIT

Maturity when described: Firm ripe, Jun. 22, 2001.

Date of first picking: Jun. 19, 2001.

Date of last picking: Jun. 28, 2001.

Size: Uniform, medium.

*Average diameter axially*.—1⅞" [47.6 mm.].

*Average diameter across suture plane*.—2½" [63.5 mm.].

*Typical weight*.—4.66 ounces [132 grams].

Form: Uniform, symmetrical, oblate, compressed axially.

*Longitudinal section form*.—Elliptical.

*Transverse section through diameter*.—Round.

Suture: An inconspicuous line extending from the base to the pistil point with some shallow grooving near the base.

Ventral surface: Rounded.

Lips: None.

Cavity: Flaring, elongated in the suture plane, suture showing on one side, Brilliant yellow [83. brill.Y] stem markings typical.

*Depth*.—7/16" [11.1 mm.].

*Breadth*.—1" [25.4 mm.].

Base: Slightly cuneate to truncate.

Apex: Truncate.

Pistil point: A moderate orange yellow [71. m.OY] dot on a flat surface.

Stem: Medium.

*Average length*.—9/16" [14.3 mm.].

*Average width*.—⅛" [3.2 mm.].

Skin:

*Thickness*.—Medium.

*Surface*.—Smooth.

*Tenacity*.—Tenacious to flesh.

*Astringency*.—Moderate.

*Tendency to crack*.—Slight in wet season.

*Color*.—Deep red [13. deep R], Brilliant yellow [83. brill.Y] where sun protected, numerous very small Moderate orange yellow [71. m.OY] freckles throughout.

*Bloom*.—Abundant.

Flesh:

*Color*.—Brilliant yellow [83. brill.Y] from skin to stone.

*Surface of pit cavity*.—Light yellow [86. l.Y] fibers breaking when twisted from the stone.

*Amygdalin*.—Moderate.

*Juice*.—Abundant, rich.

*Texture*.—Spongy, meaty.

*Fibers*.—Abundant, fine.

*Ripens*.—Slightly earliest toward the apex.

*Flavor*.—Mild with moderate acid, averaging 14 brix.

*Aroma*.—Slight.

*Eating quality*.—Good.

STONE

Type: Clingstone.
Form: Oval.
Base: Straight.
Apex: Obtuse, with an average angle of 115 degrees.
Sides: Equal.
Surface: Slightly rough.
Ridges: One characteristic vertical ridge extending from the base to the apex bisecting each side.
Color: Moderate orange yellow [71. m.OY] when first removed.
Average pit wall thickness: 1/16" [1.6 mm.].
Average width: 7/8" [22.2 mm.].
Average length: 3/4" [19.1 mm.].
Average breadth: 3/8" [9.5 mm.].
Tendency to split: Very slight.
Kernel:

*Form*.—Oval.

*Skin color*.—Pale yellow [89. p.Y] when first removed from fresh fruit.

*Pellicle color*.—Grayish brown [61. gy.Br].

*Taste*.—Bitter.

*Viable*.—Yes.

*Average width*.—7/16" [11.1 mm.].

*Average length*.—9/16" [14.3 mm.].

*Amygdalin*.—Abundant.

USE

Market: Fresh and long distance shipping.
Keeping quality: Fruit quality observed to remain in good condition in excess of 21 days in standard cold room at 36° Fahrenheit [2° Celsius].
Resistance to insects: No unusual susceptibilities noted.
Resistance to diseases: No unusual susceptibilities noted.

Other Notes

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of plum tree, substantially as illustrated and described, that is most similar to 'Santa Rosa' (unpatented) by producing red plums that harvest in late June, but is distinguished therefrom and/or an improvement thereon by being self-unfruitful, by producing an abundance of pollen, and by producing fruit that is larger in size, axially compressed in shape, and matures about 8 days earlier.

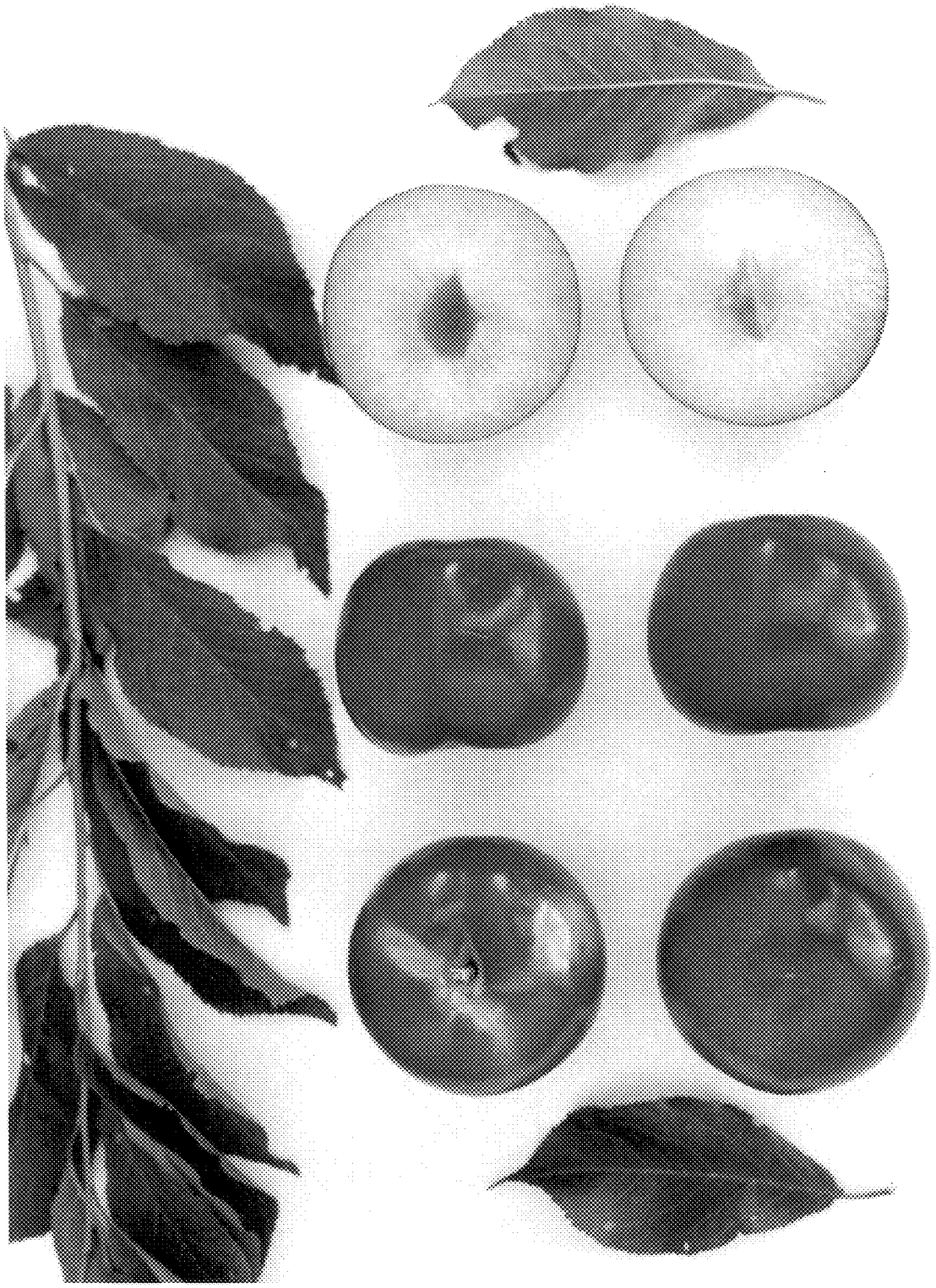

* * * * *